United States Patent [19]

Goosen

[11] Patent Number: 4,926,501

[45] Date of Patent: May 22, 1990

[54] DISPOSABLE ANTERIOR LOWER LEG GUARD

[76] Inventor: Carl C. Goosen, 2415 Shoreham Rd., Orlando, Fla. 32803

[21] Appl. No.: 274,350

[22] Filed: Nov. 21, 1988

[51] Int. Cl.⁵ .................... A41D 13/06; A41D 13/08
[52] U.S. Cl. .................................................. 2/22; 2/16
[58] Field of Search .............................. 2/22, 23, 16, 2

[56] References Cited

U.S. PATENT DOCUMENTS

| | | | |
|---|---|---|---|
| 1,801,437 | 4/1931 | Lown et al. | 2/22 |
| 2,338,424 | 1/1944 | Giardini | 2/22 |
| 2,544,065 | 3/1951 | Carr | 2/22 |
| 3,189,919 | 6/1965 | Chase | 2/16 |
| 3,446,880 | 5/1969 | Enicks | 2/2 X |
| 4,001,953 | 1/1977 | Fugere | 2/22 |
| 4,306,315 | 12/1981 | Castiglia | 2/22 |
| 4,497,070 | 2/1985 | Cho | 2/22 |
| 4,665,562 | 5/1987 | Winer | 2/22 |
| 4,669,126 | 6/1987 | Jones | 2/22 |
| 4,756,026 | 7/1988 | Pierce | 2/22 |

FOREIGN PATENT DOCUMENTS 2743741 9/1977 Fed. Rep. of Germany ............ 2/22

Primary Examiner—Werner H. Schroeder
Assistant Examiner—Sara M. Current
Attorney, Agent, or Firm—Arthur W. Fisher, III

[57] ABSTRACT

A disposable anterior lower leg guard to reduce injury to the anterior lower leg area of a patient comprising an inner corrugated shock absorbing protective member disposed within an outer relatively soft enclosure to be worn over and protect the anterior leg area of a patient.

3 Claims, 1 Drawing Sheet

DISPOSABLE ANTERIOR LOWER LEG GUARD

BACKGROUND OF THE INVENTION

1. Field of the Invention

A disposable anterior lower leg guard configured to reduce injury to the anterior lower leg area of a patient.

2. Description of the Prior Art

Numerous patients are subject to injury to the skin, subcutaneous tissue overlying the anterior and lateral aspect of the bony tibial surface. These patients most often include individuals confined to wheelchairs; elderly patient group with instability of gait; history of previous injury to the lower legs; healing leg infections or injuries; "active" bedridden patients; patients with any central nervous system disease or head injury; paraplegics; patients with peripheral arteriosclerotic cardiovascular disease with compromised lower leg circulation; status post cerebral vascular accident patients; patients with venous disease or venous hypertension; elderly group who frequently need a cane, wheelchair, crutches, or walker and status post split thickness graft to the lower leg.

Such injuries usually result from a direct blow to the lower leg. Since patients are generally older and infirmed with multiple organ system disease, they frequently have less than optimal healing capabilities. Thus there is often poor wound healing to the injured area of the lower leg and subsequent wound infection may require additional medications, antibiotics, nursing care, surgery, and frequent skin grafting.

U.S. Pat. No. 4,484,360 shows a shin guard having a rigid outer shell of polyurethane with a polyurethane foam backing. having the profile of the recess to be made. An oblong recess formed in the foam backing is centered over the shin bone or tibia. A dense, modified polyurethane is then cast in the oblong recess.

U.S. Pat. No. 4,306,315 discloses a shin guard comprising an elastic generally tubular member configured to tightly surround the lower leg of a wearer and an elongated substantially rigid member shaped to substantially conform to the contour of the shin of the wearer. The elastic tubular member has a first retaining means for retaining the substantially rigid member in a predetermined position between the elastic tubular member and the shin of the wearer. A second retaining means extends from the elastic tubular member to retain the elastic tubular member at a predetermined position of the leg of the wearer.

U.S. Pat. No. 4,497,070 shows a unitary leg and foot protective device of soft energy absorbing material comprising a lower portion to cover the top and sides of the foot of the wearer, a middle portion for covering the front and sides of the ankle of the wearer and an upper portion covering the skin of the wearer.

U.S. Pat. No. 4,001,953 discloses a protective gaiter which extending from a wearer's instep to immediately below the knee. A portion of the gaiter forms a completely closed pocket containing an energy-absorbing pad. The pocket and pad are both elongated, covering substantially the length of the gaiter, and include a concavely shaped bottom edge to position reprotective gait around the wearer's instep so that it fits over and protects the wearer's shinbones as well as covering many of the major bones and muscles of the wearer's leg.

U.S. Pat. No. 3,465,364 shows a protective pad having a flexible shock-absorbing member shaped to form a shin guard be worn under a knit sock or stocking and held in place by interlocking of split loops carried by the pad.

Other examples of prior art are found in U.S. Pat. Nos. 1,479,883; 2,779,108; 3,189,919; 3,888,244; 4,008,531; and 4,665,562.

SUMMARY OF THE INVENTION

The present invention relates to a disposable anterior lower leg guard to reduce injury to the anterior lower leg area of a patient.

Specifically, the disposable anterior lower leg guard comprises an inner corrugated shock absorbing protective member disposed within an outer relatively soft enclosure to be worn over and protect the anterior lower leg area of the patient.

The inner corrugated shock absorbing protective member comprises an elongated outer protective panel and an elongated inner corrugated shock absorbing section each including an arcuate concave recess formed on the lower end portion thereof to accommodate ankle and foot movement.

The outer relatively soft enclosure comprises an inner and outer enclosure element cooperatively forming a pocket therebetween to receive an operatively retain the inner corrugated shock absorbing protective member therebetween. An upper and lower attachment means are formed on the upper and lower portions of the outer relatively soft enclosure respectively to detachably attach the disposable anterior lower leg guard to the anterior lower leg area of a patient.

In use, the disposable anterior lower leg guard is attached to the lower leg area of at least one leg of the patient with the upper an lower attachment means such that the inner corrugated shock absorbing protective member covers the anterior lower leg area to protect the patient's leg.

The invention accordingly comprises the features of construction, combination of elements, and arrangements of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which.

Similar reference characters refer to similar parts throughout the several views of the drawings.

DETAILED DESCRIPTION OF THE PREFERRED EMBODIMENT

The present invention relates to a disposable anterior leg guard generally indicated as 10 to reduce or substantially eliminate injury to the anterior lower leg area 12 of a patient.

Unfortunately, there are many patients at risk of injuries to the lower limbs. High risk groups include patients confined to wheelchairs; elderly patients group with instability of gait; patients with history of previous injury to the lower legs; patients with healing leg infections or injuries; "active" bedridden patients; patients with any central nervous system disease or head injury; paraplegics; patients with peripheral arteriosclerotic cardiovascular disease with compromised lower leg circulation; status post cerebral vascular accident patients; patients with venous disease or venous hypertension; elderly patients who frequently need a cane, wheelchair, crutches, or walker and post split thickness graft to the lower leg.

Injury to the lower legs of such patients often result in complications and infections because of reduced healing capabilities.

The instant invention provides an inexpensive, disposable, comfortable, easily applied, safe and durable device.

Specifically the disposable anterior leg guard 10 comprises an inner corrugated shock absorbing protective member generally indicated as 14 disposed within an outer relatively soft enclosure generally indicated as 16 to be worn over and protect the anterior lower leg area 12 of the patient.

Figure 4:
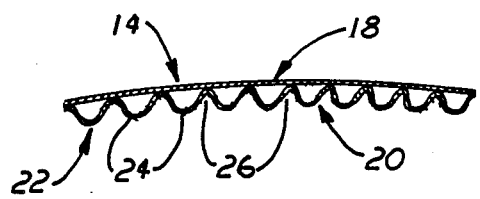
FIG. 4 is a partial cross-sectional top view of the disposable anterior lower leg guard.

As best shown in FIG. 4, the inner corrugated shock absorbing protective member 14 comprises an elongated outer protective panel and elongated inner shock absorbing section generally indicated as 18 and 20 respectively. The elongated inner shock absorbing section 20 comprises an inner shock absorbing member generally indicated as 22 including a plurality of ridges and troughes each indicated as 24 and 26 respectively. As such, the inner corrugated shock absorbing protective member 14 is pliable in one direction.

Figures 1, 2, 3:
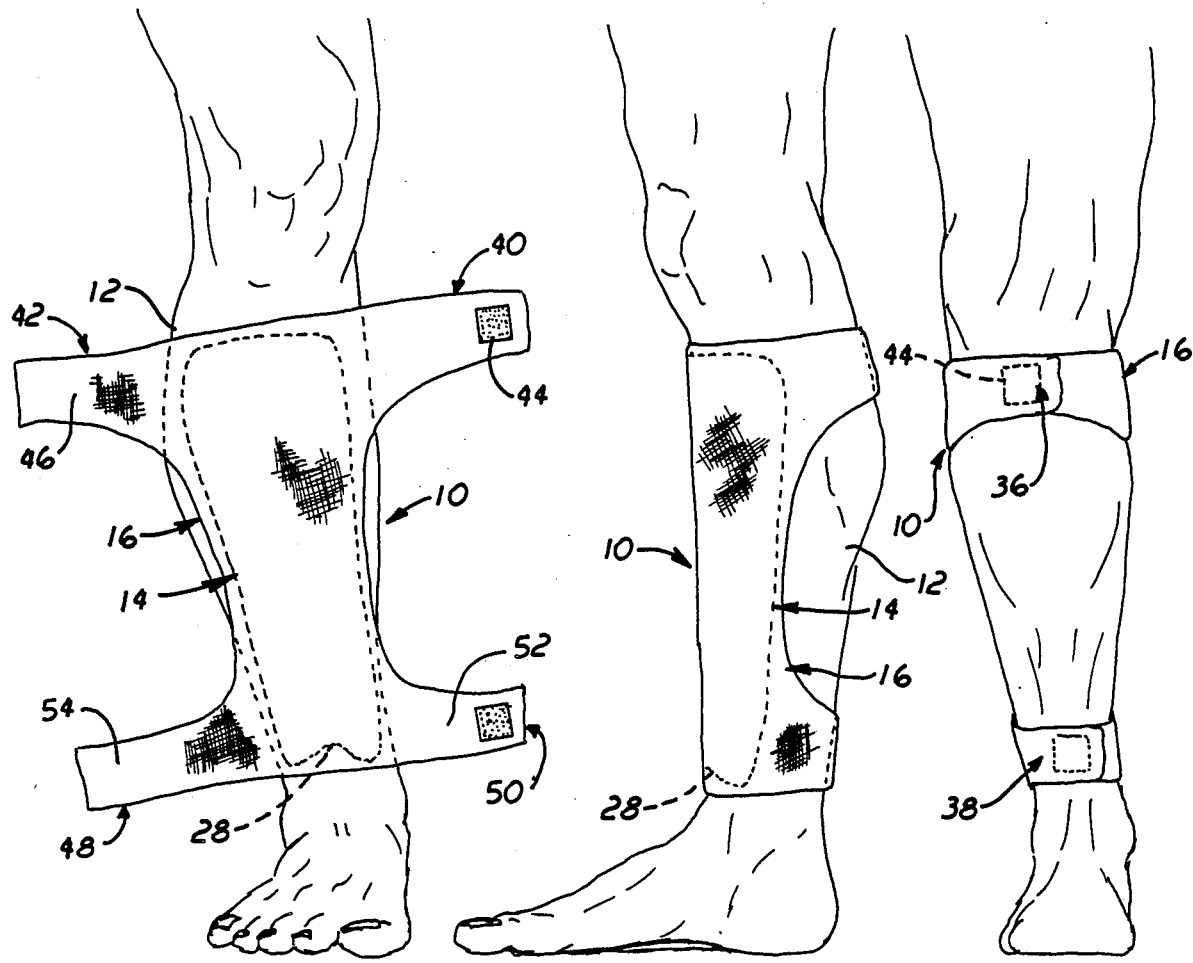
FIG. 1 is a front view of the disposable anterior lower leg guard.
FIG. 2 is a side view of the disposable anterior lower leg guard.
FIG. 3 is a rear view of the disposable anterior lower leg guard.

As best shown in FIGS. 1 and 2, the elongated inner shock absorbing section 20 includes an arcuate concave recess 28 formed on the lower portion thereof to accommodate ankle and foot movement.

The outer relatively soft enclosure 16 comprises an inner and outer enclosure element indicated as 30 and 32 respectively cooperatively forming a pocket 34 therebetween to receive and operatively retain the inner corrugated shock absorbing protective member 14 therebetween. An upper and lower attachment means generally indicated as 36 and 38 respectively are formed on the upper an lower portions of the outer relatively soft enclosure 16 to detachably attach the disposable anterior lower leg guard 10 to the anterior lower leg area 12 of the patient. The upper attachment means 36 comprises a first and second upper strap element indicated as 40 and 42 respectively having a first and second upper fastener element indicated as 44 and 46 respectively formed thereon to selectively engage each other to detachable attach the upper attachment means 36 of the disposable anterior lower leg guard 10 to the upper portion of the patient's anterior lower leg area 12. The lower attachment means 38 comprises a first and second lower strap element indicated as 48 and 50 respectively having a first and second lower fastener elements indicated as 52 and 54 respectively formed thereon to selectively engage each other to detachably attach the lower attachment means 38 of the disposable anterior lower leg guard 10 to the lower portion of the patient's anterior lower leg area 12. The first and second upper fastener elements 44 and 46, and the first and second lower fastener elements 52 and 54 may comprise Velcro elements, snaps or other suitable fasteners.

In use, the disposable anterior lower leg guard 10 is attached to the lower leg area of at least one leg of the patient with the upper and lower attachment means 36 and 38 such that the inner corrugated shock absorbing protective member 14 covers the anterior lower leg area 12 to protect the patient's lower leg.

Since the inner corrugated shock absorbing protective member 14 and outer relatively soft enclosure 16 are constructed of biodegradable material such as cardboard and non-woven material respectively, the disposable anterior lower leg guard 10 is biodegradable.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A disposable anterior lower leg guard to reduce injury to the anterior lower leg area of a patient comprising an inner shock absorbing protective member including an elongated outer protective panel and an elongated inner corrugated shock absorbing section, said elongated inner corrugated shock absorbing section comprising an inner shock absorbing member including a plurality of ridges and troughes disposed within an outer relatively soft enclosure including an inner and outer enclosure element cooperatively forming a pocket therebetween to receive and operatively retain said inner shock absorbing protective member therebetween to be worn over and protect the anterior lower leg area of the patient, and an upper and lower attachment means formed on the upper and lower portion of said outer relatively soft enclosure to detachably attach said disposable anterior leg guard to the anterior lower leg area of a patient, said elongated outer protective panel and said elongated inner corrugated shock absorbing section each including an arcuate concave recess formed on the lower end portion thereof to accommodate ankle and foot movement.

2. The disposable anterior lower leg guard of claim 1 wherein said the upper attachment means comprises a first and second strap element having a first and second upper fastener element formed respectively thereon to selectively engage each other to detachable attach said upper attachment means to the upper portion of the patient's and said lower attachment means comprises a first and second lower strap element having a first and second lower fastener element formed respectively thereon to selectively engage each other to detachably attach said lower attachment means to the lower portion of the patient's anterior lower leg area.

3. The disposable anterior lower leg guard of claim 1 wherein said inner shock absorbing protective member and said outer relatively soft enclosure each comprises a biodegradable material.

* * * * *